United States Patent [19]

Hicks et al.

[11] Patent Number: 5,130,172
[45] Date of Patent: Jul. 14, 1992

[54] LOW TEMPERATURE ORGANOMETALLIC DEPOSITION OF METALS

[75] Inventors: Robert F. Hicks; Herbert D. Kaesz, both of Los Angeles, Calif.

[73] Assignee: The Regents of the University of California, Berkeley, Calif.

[21] Appl. No.: 428,245

[22] Filed: Oct. 26, 1989

Related U.S. Application Data

[63] Continuation-in-part of Ser. No. 260,799, Oct. 21, 1988, abandoned.

[51] Int. Cl.$^5$ .................. B05D 3/06; B05D 5/12; C23C 16/00
[52] U.S. Cl. .................. 427/252; 427/53.1; 427/54.1; 427/124; 427/125; 427/99
[58] Field of Search .............. 427/53.1, 250, 252, 427/99, 229, 226, 123, 124, 125, 54.1; 428/457, 450, 401

[56] References Cited

U.S. PATENT DOCUMENTS

| | | | |
|---|---|---|---|
| 3,256,109 | 6/1966 | Berger | 427/229 |
| 4,006,047 | 2/1977 | Brummett et al. | 427/229 |
| 4,206,540 | 6/1980 | Gould | 427/84 |
| 4,322,453 | 3/1982 | Miller | 427/89 |
| 4,328,080 | 5/1982 | Harris | 427/115 |
| 4,353,935 | 10/1982 | Symersky | 427/124 |
| 4,830,880 | 5/1989 | Okubi et al. | 427/229 |
| 4,880,670 | 11/1989 | Ebril | 427/229 |
| 4,882,206 | 11/1989 | Ebril | 427/229 |
| 4,948,623 | 8/1990 | Beach et al. | 427/53.1 |

OTHER PUBLICATIONS

Groshart, Earl, "Metalizing Nonconductors—Vapor Plating," Aug., 1972, pp. 49–54, Metal Finishing.
Rand, Myron J., "Chemical Vapor Deposition of Thin-Film Platinum," May, 1973, pp. 686–692, Electrochem Soc.
Gozum, John E. et al., "'Tailored' Organometallics as Precursors for the Chem. Vapor Deposition . . . " 1988, pp. 2688–2689, J. Am. Chem. Soc. vol. 110, No. 8.
Egger, K. W., "Cyclopentadienyl-Metal Complexes II. Mass Spectrometric and Gas Phase Kinetic Studies . . . " 24 (1970), pp. 501–506, J. Organometal. Chem.
Miller, Timothy M. et al., "Heterogeneous, Platinum--Catalyzed hydrogenation of (Diolefin)dialkylplatinum-(II) . . . " 1988, pp. 3146–3156, J. Amer. Chem Soc. vol. 110 #10.
Miller, Timothy M. et al., "Deuterium-Labeling Experiments Relevant to the Mechanism of Platinum-Catalyzed . . . " 1988, pp. 3156–3163, J. Amer. Chem Soc. vol. 110 #10.
Miller, Timothy M. et al., "Isotopic Exchange Reactions Occurring in the Hydrogenation of . . . " 1988, pp. 3164–3170, J. Amer. Chem. Soc. vol. 110 #10.
Kaplin, Yu. A. et al., "Decomposition of Nickelocene in Presence of Hydrogen" Jan., 1980, pp. 118–121, UDC.
Saraswat, K. C. et al., "Selective CVD of Tungsten for VSLI Technology," 1984, VSLI Science & Technology, pp. 409–419.
Bindra, Perminder et al., "Mechanisms of Electroless Metal Plating," 1985, pp. 2581–2625, J. Electrochem Soc. Electrochemical Science and Technology, Nov. vol. 132 #11.
Koplitz, Lynn Vogel et al., "Gas Phase Laser Photodeposition of Platinum at Atmospheric Pressure and Room Temperature from CpPt(CH$_3$)$_3$".
Ho, P. S. et al., ed. *Thin Films and Interfaces* "Metallization for Very-Large Scale Integrated Circuits," Nov. 1981, pp. 379–395, by P. B. Ghate Proc. of the Materials Res. Soc.
Girolami, Gregory S. et al., "Organometallic Route to the Chemical Vapor Deposition of Titanium Carbide . . . " 1987, pp. 1579–1580, J. Amer. Chem. Soc. vol. 109.
Schroder, H. et al., "Investigation of UV-Laser Induced Metallization: Platinum from Pt(Pf$_3$)$_4$" 1985, pp. 227–233, Appl. Phys. A38.
Thomas, Richard R. et al., "Vapor Phase Deposition of Palladium for Electroless Copper Plating," Apr. 28, 1987, pp. 1–8, IBM Research Report RC 12719.
Eizenberg, M., "Applications of Thin Alloy Filsm in Silicide Contacts," 1984, pp. 348–360, VLSI Science and Technology, vol. 84-7, ed. Bean et al.
Girolami, Gregory S. et al., "The Organometallic Route to the Preparation of Metal Carbides and Borides by CVD," Inor., No. 429.
Houle, F. A., et al., "Surface Processes Leading to Carbon Contamination of Photochemically Deposited Copper Films", Nov./Dec. 1986, A4(6) pp. 2452–2458, J. Vac Sci.
Stauf, G. T. et al., "Iron and Nickel Thin Film Deposition Via Metallocene Decomposition," Thin Solid Films, 153 (Mar. 1987) 421–430.

*Primary Examiner*—Marianne Padgett
*Attorney, Agent, or Firm*—George F. Bethel; Patience K. Bethel

[57] ABSTRACT

A process for coating metal on a substrate. The process uses organometallic compounds such as (trimethyl)(cyclopentadienyl) platinum in the presence of a reducing fluid such as hydrogen gas to produce high purity films capable of selective deposition on substrates containing, for example, tungsten and silicon. The films are deposited using chemical vapor deposition (CVD) or gas phase laser deposition. The invention also comprises devices made from the process of the invention.

30 Claims, No Drawings

LOW TEMPERATURE ORGANOMETALLIC DEPOSITION OF METALS

This application is a continuation in part of application Ser. No. 07/260,799 filed Oct. 21, 1988, now abandoned.

BACKGROUND OF THE INVENTION

1. Field of the Invention

This invention relates to methods of coating substrates with metals and devices made using the methods of the invention.

2. Description of Related Art

Thin coatings of metals are vitally important in many industries. The microelectronics industry, for example needs thin coatings of metals to make integrated circuits, where size of the device is critical to performance. In catalysis, metals play an important function in automobile exhaust catalysis and in many other reactions. Since some catalysts, such as platinum, can be extremely expensive, a thin coating of the catalytic metal on the surface of the catalytic body is desirable.

In many applications of thin metal films, selective coating is required. For example in the microelectronics industry, a metal, such as platinum, must be selectively coated on a semiconductor surface to provide interconnects to the various circuit elements. If the wrong circuit elements are connected, then the whole semiconductor chip may become worthless.

In some applications of metal coating, high purity of the deposited metal is required. For example in catalysis, the metal catalyst can be poisoned by impurities. And, in the microelectronics industry, impurities can damage a circuit element or the function of an interconnecting link between the various circuit elements.

In some applications, a thorough coating of the metal is needed. For example in the microelectronics industry, if a metal is designed to separate two other layers from each other, a less than complete coating could damage the circuit or cause a short-circuit.

Several methods have been proposed for placing a thin coating of metal on a substrate, including precipitation from liquid solution, sputtering, and chemical vapor deposition (CVD). Liquid solution precipitation does not always provide selective deposition or the proper degree of purity, and sputtering does not always provide a thorough coating, since it is restricted to line-of-sight deposition and may miss nooks and crannies in the substrate. In addition, sputtering often requires a mask to achieve selective deposition, or the extra metal must be etched away in a subsequent treatment, which results in loss of a potentially expensive metal.

CVD, on the other hand, can provide selective deposition under the right circumstances. Moreover, since it does not rely on line-of-sight deposition techniques, it will provide a thorough coating on a substrate containing nooks and crannies. CVD, however, suffers from problems with obtaining satisfactory purity levels in the metal. Chemical vapor deposition involves decomposing a volatile compound containing a metal on a surface that is typically heated. There are at least three ways to accomplish the decomposition of the volatile metal compound: reduction, thermal decomposition and displacement. Groshart, E., "Metalizing Nonconductors," *Metal Finishing*, p.49 (August 1972).

In reduction, hydrogen or some other reducing gas is exposed to the volatile metal compound either during or after deposition on the substrate. The hydrogen reacts with the non-metal portion of the compound, leaving the metal behind on the substrate. In thermal decomposition, the substrate is heated, and the volatile compound reacts with itself to form a nonmetallic material that leaves the substrate and a metal that stays. In displacement, a material already present on the surface of the substrate reacts with the volatile compound and "changes place" with the metal to be deposited.

In each of these techniques, however, the purity of the deposited metal can be affected by the other components of the volatile compound and by any contaminant in the system. For example when platinum acetylacetonate, $Pt(CO)_2(Cl_2)$, and platinum trifluorophosphine were tried on a substrate-containing silicon, each platinum coating showed signs of contamination by other elements. Rand, M., "Chemical Vapor Deposition of Thin-Film Platinum," *J. Electrochem. Soc. Solid-State Science and Technology*, 120, 686 (1973).

One potential source of volatile compounds for thin metal films for CVD is organometallics. These compounds provide high growth rates, ease of process control and generally higher purity than some other volatile compounds. See Gozum, J. et al., "'Tailored' Organometallics as Precursors for the Chemical Vapor Deposition of High-Purity Palladium and Platinum Thin Films," *J. Am. Chem. Soc.*, 110, 2688 (1988). In that article, bis(allyl)palladium, bis(2-methylallyl) palladium and (cyclopentadienyl)(allyl)palladium were reported to be tested for CVD at 250° C. and 0.0001 torr. The article reported that the cyclopentadienyl compound had about 5% residual carbon as a contaminant. The article also reported that the cyclopentadienyl complex $CpPtMe_3$ [(cyclopentadienyl)(trimethyl)platinum] "yield[s] high-quality Pt films under similarly mild (250° C., $10^{-4}$ torr) conditions." That article, however, did not report on the necessity of a reducing gas, especially hydrogen, to obtain high purity. Titanium carbide (TiC) films have also been deposited using tetraneopentyltitanium ($Ti[CH_2C(CH_3)_3]_4$) at approximately 150° C. There was enough carbon present after CVD to account for a separate TiC phase in the deposited material.

Organometallic compounds have also been evaluated for other purposes. For example, in Egger, K., "Cyclopentadienyl-Metal Complexes II. Mass Spectrometric and Gas Phase Kinetic Studies on the Thermal Stability and the Structure of $(CH_3)_3Pt-C_5H_5$," *J. Organometallic Chemistry*, 24, 501 (1970), testing to determine the structure of cyclopentadienyltrimethylplatinum(iv) was reported. The article concluded that the cyclopentadienyl group was Pi bonded. Analysis of the hydrogenation of (1,5 cyclooctadiene) dimethylplatinum has also been reported. Miller, T. et al., "Heterogeneous, Platinum-Catalyzed Hydrogenation of (Diolefin)dialkylplatinum(II) Complexes: Kinetics," *J. Am. Chem. Soc.*, 3146 (1988) (and two subsequent articles by the same author). Hydrogenation of nickelocene $((C_5H_5)_2Ni)$ has also been reported. Kaplin, Y. et al., "Decomposition of Nickelocene in Presence of Hydrogen," UDC 547.1'174, c. 1980 Plenum Publishing Corp., translated from *Zhurnal Obshchei Khimii*, 50, 118 (1980). None of these articles, however, report any special benefits of using the compounds in CVD.

Thus, there is presently a need in the art for an organometallic compound useful in CVD of metals that does not contaminate the deposited metal with impurities and that uses a reducing gas, such as hydrogen, to remove the organic ligands during or after deposition.

SUMMARY OF THE INVENTION

The invention comprises a method for depositing a thin metal film onto a substrate using chemical vapor deposition or gas phase laser photodeposition. The metal is present as a volatile organometallic compound, such as cyclopentadienyl(trimethyl)platinum, and produces a highly pure thin metal film upon reduction of the metal. The film may be deposited over the entire surface of a substrate or may be selectively deposited, depending on the nature of the underlying substrate and the deposited metal.

The invention also comprises devices made by using the method of the invention.

DESCRIPTION OF THE PREFERRED EMBODIMENTS

In accordance with the invention, the chemical vapor deposition may use any procedure normally followed in CVD of metals. The preferred technique, however, comprises introduction of an organometallic compound of sufficient volatility into a reaction vessel containing a substrate, deposition of the organometallic compound onto the substrate and reduction or elimination of the organic ligands by reaction with a reducing gas, and preferably heat.

In the preferred method, a gaseous organometallic compound is introduced into a sealed vessel along with a substrate. The substrate should preferably be heated, for a silicon substrate to approximately 150° C. The compound is preferably introduced into the reaction vessel as a gaseous mixture along with an inert gas. The relative amounts of inert gas and compound can be adjusted by those skilled in the art to control the rate of deposition and the amount of compound deposited from the gas mixture. In the preferred method, hydrogen, a reducing gas, may be introduced into the sealed vessel along with the compound and inert gas mixture, but the hydrogen gas may also be introduced before or after deposition of the organometallic compound. The deposition and removal of the organic ligand may be followed by other steps, such as etching, if necessary to the particular application.

The organometallic compound generally has the formula $L_nMR_m$, where L is hydrogen (H), ethylene ($C_2H_4$), allyl ($C_3H_5$), methylallyl ($CH_3C_3H_4$), butadienyl ($C_{hd\ 4}H_6$), pentadienyl ($C_5H_8$), cyclopentadienyl ($C_5H_5$), methylcyclopentadienyl ($CH_3C_5H_4$), cyclohexadienyl ($C_6H_8$), hexadienyl ($C_6H_{10}$), cycloheptatrienyl ($C_7H_8$), or any of the ligands discussed below, n is a number from 0 to 3, M is the selected metal, R is methyl ($CH_3$), ethyl ($C_2H_5$), propyl ($C_3H_7$), butyl ($C_4H_9$) or carbon monoxide (CO), or any of the ligands disclosed below, and m is a number from 0 to an integer sufficient to complete the coordination. Although not all of the following compounds have been tested for use in the invention, they have all been made in the art or are disclosed here, and would be expected to be suitable organometallic compounds for use in the invention. In the list below, Cp means cyclopentadienyl; Me is methyl; Ch is cyclohexadienyl; and MeCp is methylcyclopentadienyl; (1) $CpPtMe_3$; (2) $CpPt(allyl)$; (3) $CpPt(methylallyl)$; (4) $MeCpPt(Methylallyl)$; (5) $CpPt(CO)$ $CH_3$; (6) $MeCpPt(CO)CH_3$; (7) bisallylPd; (8) (methylallyl)Pd(allyl); (9) the palladium compounds as set forth in Gozum, J. et al., "'Tailored' organometallics as Precursors for the Chemical Vapor Deposition of High-Purity Palladium and Platinum Thin Films," *J. American Chem. Soc.*, 110, 2688 (1988) (10) $(CH_3C_5H_4)PtMe_3$; (11) $(C_3H_5)_3Rh$; (12) $(C_3H_5),Ir$; (13) CpIr(hexadiene) ; (14) $(C_5H_5)Ir(C_6H_8)$; (15) $(C_5(CH_3)_5)Ir(ethylene)_2$; (16) $(C_5H_7)Ir(C_8H_8)$; (17) $HRe(CO)_5$; (18) $(CH_3C_5H_4)_2Ni$; (19) $(C_5H_5)Co(CO)_2$; (20) $(C_5H_5)CoCp$; (21) $(C_5H_5)CoCh$; (22) $(CH_3C_5H_4)Co$ (MeCp); (23) (cyclobutadienyl)(cyclopentadienyl) cobalt, $C_4H_3CoC_5H_5$; (24) bis(cyclopentadienyl)cobalt, $(C_5H_5)_2Co$; (25) bis(methylcyclopentadienyl)cobalt, $(CH_3C_5H_4)_2$ Co; (26) bis(cyclopentadienyl) cobalt, $C_5H_5CoC_5H_5$; (27) bis(methylcyclopentadienyl) cobalt, $(CH_3C_5H_4)_2Co$; (28) cyclopentadienyl(1,3-hexadienyl)-cobalt, $C_5H_5CoC_6H_7$; (29) (cyclopentadienyl)(5-methyl-cyclopentadienyl) cobalt, $C_5H_5CoC_5H_4CH_3$; (30) bis(ethylene) (pentamethylcyclopentadienyl) cobalt, $(CH_3)_5C_5Co(C_2H_2)_2$; (31) triallylchromium, $(C_3H_4)_3Cr$; (32) bis(cyclopentadienyl) chromium, $(C_5H_5)_2Cr$; (33) (cycloheptatrienyl) (cyclopentadienyl)chromium, $C_7H_7CrC_5H_5$; (34) bis(cyclopentadienyl)iron, $(C_5H_5)_2Fe$; (35) (2,4-cyclohexadienyl)(cyclopentadienyl)iron, $C_6H_7FeC_5H_5$; (36) (cyclopentadienyl)-(methylcyclopentadienyl)iron, $C_5H_5FeC_5H_4CH_3$; (37) bis(methylcyclopentadienyl)iron, $(CH_3C_5H_4)_2Fe$; (38) (cycloheptatrienyl)(cyclopentadienyl)manganese, $C_5H_5MnC_7H_8$; (39) (benzene)(cyclopentadienyl)manganese, $C_5H_5MnC_6H_6$; (40) dihydrobis(cyclopentadienyl)molybdenum, $(C_5H_5)_2MoH_2$; (41) bis(cyclopentadienyl) (ethylene)molybdenum, $(C_5H_5)_2MoC_2H_2$; (42) tris(butadienyl)molybdenum, $(C_4H_4)_3Mo$; (43) dicyclopentadienyltrihydroniobium, $(C_5H_5)_2NbH_3$; (44) bis(cyclopentadienyl)niobium-borohydride, $(C_5H_5)_2NbH_2BH_2$; (45) bis(cyclopentadienyl)hydro(ethylene)niobium, $(C_5H_5)_2NbHC_2H_2$; (46) bis(cyclopentaldienyl)allylnibbium, $(C_5H_5)_2NbC_3H_4$; (47) ethenylosmocene, $C_5H_5OsC_5H_4CHCH_2$; (48) 1,1'-dimethylosmocene, $(C_5H_4CH_3)_2Os$; (49) ethylosmocene, $C_5H_5OsC_5H_4CH_2CH_3$; (50) bis(cyclopentadienyl)hydridorhenium, $(C_5H_5)_2ReH$; (51) hexamethylrhenium, $(CH_3)_6Re$; (52) cyclopentadienyl(methylcyclopentadienyl)ruthenium, $C_5H_5RuC_5H_4CH_3$; (53) ruthenocanylacetylene, $C_5H_5RuC_5H_4CCH$; (54)ethenylruthenocene $C_5H_5RuC_5H_4CHCH_2$; (55) bis(methylcyclopentadienyl)ruthenium, $Ru(CH_3C_5H_4)_2$; (56) ethylruthenocene, $C_5H_5RuC_5H_4CH_2CH_3$; (57) pentamethyltantalum, $Ta(CH_3)_5$; (58) bis(cyclopentadienyl)trihydrotantalum, $C_5H_5)_2TaH_3$; (59) bis(cyclopentadienyl) trimethyltitanium, $(C_5H_5)_2Ti(CH_3)_3$; (60) titanocene borohydride, $(C_5H_5)_2TiH_2BH_2$; bis(cyclopentadienyl)-dimethyltitanium, $C_5H_5)_2Ti(CH_3)_2$; (61) bis(cyclopentadienyl)methylvanadium, $(C_5H_5)_2VCH_3$; (62) 1,1'-dimethylvanadocene, $(C_5H_4CH_3)_2V$; (63) bis(2,4-dimethylpentadienyl) vanadium, $C_5H_3(CH_3)_2)_2V$; (64) bis(cyclopentadienyl)dihydrotungsten, $(C_5H_5)_2WH_2$; 65) trisbutadienyl-tungsten, $(C_4H_5)_3W$; and (66) bis(cyclopentadienyl(butadienyl)zirconium, $(C_5H_5)_2ZrC_4H_4$.

The metal portion of the organometallic compound of the invention can be any metal that readily cycles between at least two oxidation states and forms hydrocarbon complexes. A metal can be said to "readily" cycle between two oxidation states if an organometallic compound made from the metal can undergo reductive elimination with hydrogen gas at temperatures below 300 degrees C. Typically, these metals include those having atomic numbers from 22-29, 40-47 or 72-79.

The preferred metals, however, have atomic numbers from 25-29, 42-47 and 72-79. Particularly preferred metals include W, Cu, Ag, Au, Pt, Pd, Co, Rh, Ir, and Ni.

In addition, two classes of organometallic copper compounds are suitable as precursors for formulation of CVD copper films. The first class has the following formula:

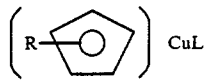

wherein R and L have the following definitions: (a) if R is H, Me, or Et, then L may be $PMe_3$ or $PEt_3$; (b) if R is H or Me, then L may be Bis(trimethylsilyl)acetylene or 1,1,2,2-tetramethylethylene; and (c) if R is H, Me, or Et, the L may be CNMe, CNEt, $CNPr^i$ (isocyano-1-methylethane) or $CNBt^t$ (isocyano-1,1-dimethylethane). The second class of copper compounds has the formula:

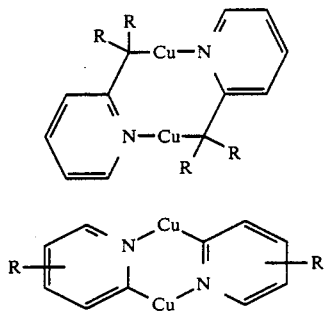

wherein R is Me, Et, $Pr^i$, $Bt^t$, or $Si(Me_3)$.

The selected metal is combined with an organic ligand to form a compound with sufficient volatility to have a significant vapor pressure at mild temperatures. Mild temperatures are preferably between room temperature and about 100° C. But, the temperature may vary from this range depending on the application of the process and the nature of the organometallic compound selected. A significant vapor pressure is about 0.001 torr or greater at 25°-100° C., and most preferably between 1 and 10 torr. Organometallic compounds with a lower vapor pressure can be within the scope of the invention, but if the vapor pressure is low, then the chemical vapor deposition process will be slowed and will be less convenient. An important factor in selecting which organometallic compound to use is to select compounds that do not leave contaminants in the metal after reduction, such as phosphorous, carbon or oxygen.

Using chemical vapor deposition, the preferred technique for removing the organic ligand from the deposited organometallic compound is reduction to form an organic gas. The preferred technique for achieving this result is by exposing the organometallic material to a reducing gas over a substrate at a sufficient temperature and pressure to cause the organic ligand to react with the gas and deposit the metal. The preferred reducing gas is hydrogen, due to its expense and due to the fact that the metal, especially platinum, may catalyze the hydrogenation reaction, but other reducing gasses may be used. Alternatively, the organometallic compound can partially decompose onto substrate at a specified temperature. Then hydrogen can be introduced to remove any remaining organic ligands.

In an alternative embodiment, elimination of the organic ligand may be accomplished by heating the substrate to allow the organic ligand to thermally decompose. If this embodiment is selected, those skilled in the art will recognize that the organic ligand should decompose entirely into gases that will not remain in the metal layer as a contaminant.

Another way to eliminate the organic ligand from the metal coating is through photodeposition. In photodeposition, an organometallic compound is deposited on a substrate and by exposure to a light source of sufficient intensity to carry out photolytic elimination of the organic ligand. Preferably, the process is carried out in the presence of a reducing gas, such as hydrogen, but depending on the organometallic compound, a reducing gas may not be necessary. The organometallic compound may be deposited simultaneously with exposure to the reducing gas and light source, or the deposition and photolytic decomposition step may be carried out sequentially. The light source may be a laser.

The invention may also be used to deposit metals onto a substrate containing two or more chemical regions on its surface selectively. For example, using $CpPtMe_3$, platinum may be deposited on a substrate of silicon, tungsten and silicon oxide. This particular deposition method is very important in preparing VLSI (Very Large Scale Integrated) circuits. Deposition of platinum on tungsten occurs at a much lower temperature than on dielectric ($SiO_2$, $Si_3N_4$) and semiconductor (Si, GaAs) surfaces. By accurately controlling the temperature of the substrate, therefore, platinum can be selectively deposited on tungsten or Si/W surfaces. Since the technology for forming Si/W contact holes using preferential deposition is known, Saraswat, K. et al., "Selective CVD of Tungsten for VLSI Technology," *VLSI Science & Technology*, 409 (1984), the invention can be used to deposit platinum onto Si/W contact holes without spilling over onto adjacent dielectric or semiconductor surfaces.

The invention may also be used to make alloys, such as PtGa metals.

The following Examples are intended to illustrate the invention but are not intended to limit the scope of the invention.

EXAMPLE 1

Preparation of Organometallics

The following organometallic compounds were prepared:
(a) $CpPtMe_3$
(b) $CpPtMe_3$
(c) $(CH_3C_5H_4)PtMe_3$
(d) $(C_3H_5)_3Rh$
(e) $(C_3H_5)_3Ir$
(f) $HRe(CO)_5$
(g) $(CH_3C_5H_4)_2Ni$
(h) $(C_5H_5)Co(CO)_2$
(i) $(C_5H_5)CoCp$
(j) $(C_5H_5)CoCh$
(k) $(CH_3C_5H_4)Co(MeCp)$ where Cp is cyclopentadienyl; Me is methyl; Ch is cyclohexadiene; and MeCp is methyl cyclopentadiene.

Compound (a) was prepared from $PtMe_3I$ and NaCp using the procedure described in Robinson, S. and Shaw, B., *J. Chem. Soc.*, 277, 1529 (1965), except that toluene was used instead of benzene as the solvent, and the reaction was started at −77° C. The yield obtained was 52%. Compound (b) was obtained using the Robinson and Shaw procedure.

Compound (c) was prepared as follows: 445 mg PtMe$_3$I in 25 ml ethyl ester dried over potassium and benzene was added dropwise at −78° C. under nitrogen to 1.5 ml of approximately 1.1M MeCpNa. The solution was slowly raised back to room temperature over 12 hours while stirring. Ethyl ether and THF were removed at −20° to −30° C., leaving an oily residue that sublimed at room temperature. A cold finger at −15° C. gave 62 mg of a yellow compound. The residue was extracted with pentane and filtrated in air. The pentane was removed at −20° C.

Compound (d) was prepared as follows: 100 mg RhCl$_3$ anhydrous was stirred in 50 ml ethyl ether dried over potassium and benzophenone and added to a ten times excess of allylMgCl (2.0M in THF (Aldrich)). After stirring for 12 hours, dry ice was added to the decomposed excess allylMgCl, and the mixture was dried under vacuum at −15° C. Pentane was then used to exhaust the residue and pentane was removed at about 5 degrees centigrade by water evaporation. After sublimation (cold finger at temperature of running water, flask at room temperature), a yellow solid formed on the cold finger.

Compound (e) was prepared as follows: 0.200 g IrCl$_3$ in 4 ml toluene was dried and added dropwise under argon gas to 3.4 ml of 2M allylMgCl in THF (Aldrich) at −78 degrees C. The black IrCl$_3$ remained undissolved. The solution was then raised to room temperature and heated on a water bath to 50° C. for 10 hours. The solution was dark and no precipitate formed. A few lumps of dry ice was added to destroy any remaining grignard reagent. Solvent was removed at 0° C. under $10^{-2}$ torr vacuum. 50 ml pentane was used to extract the product from the raw product, and the pentane was removed at 15°-20° C. and $10^{-2}$ torr to give the crude product. The crude product was then purified by sublimation at 15 torr and 50° C. with a cold finger at 10° C. for about 30 minutes.

Compounds (f)-(k) were prepared using similar procedures.

EXAMPLE 2

Use of Organometallics to Form CVD Films

Compound (a) was used to form a film on a substrate in the following manner: either glass slides or silicon wafers with (100) orientation were used as substrates. The glass slides were cleaned with acetone prior to use. The silicon substrates were degreased in trichloroethylene, acetone and isopropanol, dipped in concentrated hydrofluoric acid, rinsed in deionized water, and gently dried under argon. The substrates were held at reaction temperature in a hydrogen atmosphere for 30 minutes prior to film deposition. The deposition took place in a cold wall glass reactor. The substrates were mounted on a resistively heated pedestal and held at 180° C. during deposition. Compound (a) was vaporized at atmospheric pressure and 25° C. into a stream of flowing argon at 25 ml/min. The vapor pressure of compound (a) is 0.05 torr at 25° C. The argon-compound (a) mixture was introduced into the reactor through a port, and hydrogen gas was introduced into the reaction vessel through another port at 25 ml/min. The hydrogen, argon and compound (a) flowed over the hot substrate and reacted on the surface to form a platinum film. The rate of deposition was approximately 1 angstrom per second. Depositions were carried out for one-half to three hours, resulting in films up to several thousand angstroms thick.

The structure of the films was analyzed by x-ray diffraction, scanning electron microscopy, x-ray photoelectron and Auger spectroscopies. The sheet resistivity was measured with a 4-point probe. Film thickness was measured with a Deptak II profilmeter. Analysis of the results showed that the film was highly pure, although the film could become contaminated with oxygen and carbon after several days' ambient exposure. After argon sputtering to remove these impurities, the oxygen content of the film decreases below detection limits and the carbon contamination is less than 1 atom percent. There were no other detected impurities. In the absence of hydrogen in the reactant gases, higher concentrations of carbon contamination were detected.

Compound (c), compound (d) and compound (e) were each tested using the technique described above. Each had a similar result.

For compounds (d)-(k), the temperatures shown in Table 1 were used to deposit metals on the listed substrates. The results showed that a clean metal film was found.

TABLE 1

| Metal | Compound | Substrate | Temperature |
| --- | --- | --- | --- |
| Rh | (d) | Silicon | 120 degrees C. |
| Ir | (e) | Silicon | 100 degrees C. |
| Re | (f) | Silicon | 130 degrees C. |
| Ni | (g) | Glass | 190 degrees C. |
| Ni | (g) | Silicon | 280 degrees C. |
| Co | (h) | Silicon | >370 degrees C. |
| Co | (i) | Silicon | >370 degrees C. |
| Co | (j) | Silicon | >370 degrees C. |
| Co | (k) | Silicon | >370 degrees C. |

EXAMPLE 3

Laser Photodeposition

Crystals of compound (b) were heated to about 50° C. in a small bulb. The vapor pressure of the compound was approximately 0.33 torr. The vapor was transported to the deposition cell by a stream of argon gas at a flow rate of 2 cc/sec. Hydrogen gas was introduced into the reaction vessel in proximity to the laser beam, and gas flow was parallel to the surface of the substrate. All photolyses were carried out at atmospheric pressure with the laser beam perpendicular to the surface. The laser was a 308 nm line of a XeCl excimer laser or the 351 and 364 nm lines of an argon ion laser. The substrates were glass, fused silica, sapphire (1102), silicon (001) and GaAs (001). The single crystal silicon wafers were degreased by immersion in trichlorethylene and then rinsed in methanol and deionized water. The wafer was then twice etched for two minutes in a 1:4 solution of 30% hydrogen peroxide and concentrated sulfuric acid, rinsed in deionized water and blow dried in nitrogen.

The deposition was first carried out by irradiating a circle 1 mm in diameter with 2.6 mJ/pulse at 10 Hz using the 308 nm band. Visible mirrors formed on the substrates in about 10 minutes. The resulting films were about 1000 angstroms thick. In the absence of hydrogen, the films were black, not shiny and reflective.

Photodeposition was carried out under CW conditions with fluences of 4-5 mW/mm$^2$ at laser wave lengths of 351 and 364 nm. Using the same flow rates, mirror-like deposits were observed in about 10 minutes. Attempts were made to irradiate the substrate with visible lines (488 and 514 nm) of the argon laser, but no deposits were observed with laser fluences as high as 0.5 W/mm$^2$.

The films were analyzed using Auger electron spectroscopy which showed at most 3.5% carbon as a contaminant in the mirror-like films, but about 20% carbon in the films made in the absence of hydrogen.

The substrate was patterned using a mask and a 40 mm lens for the laser. The image was focussed below the surface of the substrate in order to minimize the focus, and hence deposition, on the cell windows. Successful patterned deposition was obtained.

During the deposition experiments, it was observed that if a preselected area of the substrate was exposed to laser irradiation in the absence of hydrogen for several minutes, but not long enough for the black film to form, only that area would form the mirror-like deposit in the presence of compound (b) and hydrogen.

EXAMPLE 4

Preparation of Organometallic Copper Precursors

The compound (MeCp)Cu(PMe$_3$) was prepared from CuI, Na(MeCp) and PMe$_3$ using the following procedure. Neat PMe$_3$ (0.912 g/12.5 mmol) was added to a toluene suspension of 1.90 g/10 mmol, in 50 ml CuI under nitrogen at room temperature with stirring. After 10 minutes, the clear, pale yellow solution was cooled to −20 degrees C., a stock THF solution of Na(MeCp) (1.04M × 10 ml) was added dropwise. After the reaction mixture was stirred at room temperature of 12 more hours, volatile materials were removed under vacuum. The residue was extracted with hexane, giving the desired compound in white crystalline form. The yield is generally over 90% (based on two preparations).

EXAMPLE 5

Formation of CVD Films Using Copper

The compound from Example 4 was used to form a film on a substrate in the following ways: (1) a glass slide or 2) a silicon wafer with (100) orientation was used as the substrate. The glass slide was cleaned with acetone prior to use. The silicon substrate was degreased in trichloroethylene, acetone and isopropanol, dipped in concentrated hydrofluoric acid, rinsed in deionized water, and gently dried under Argon. The substrates were held at reaction temperature under a hydrogen atmosphere for 30 minutes prior to film deposition. The temperature of the substrates was kept at 200 degrees C. with a resistively heated pedestal during deposition. The precursor was vaporized at 50 degrees C. into a stream of flowing argon at 25 ml/min. The stream mixture was introduced into the reactor through a port, and hydrogen gas was introduced into the reactor through another port at 25 ml/min. Deposition was carried out for 10 hours, resulting in a red copper film.

It will be apparent to those skilled in the art that various modifications and alterations may be made to the invention without departing from the scope or spirit thereof.

We claim

1. A process for coating onto a substrate at least one metal that can readily cycle between two oxidation states and is a hydrogenation catalyst capable of hydrogenating hydrocarbon ligands of an organometallic compound comprising the steps of:

(a) maintaining said substrate through the reaction at a temperature in the range of about room temperature to about 190° C.;

(b) exposing said substrate to a fluid containing at least one vaporized organometallic compound having the formula L$_n$MR$_m$, where L is hydrogen, ethylene, allyl, methylally, butadienyl, pentadienyl, cyclopentadienyl, methylcyclopentadienyl, cyclohexadienyl, hexadienyl, cycloheptatrienyl, or derivative of said compounds having at least one alkyl side chain having less than five carbon atoms, M is a metal that can readily cycle between two oxidation states and can catalyze hydrogenation of hydrocarbon ligands of said organometallic compound, R is methyl, ethyl, propyl, or butyl, n is a number from 0 to the valence of said metal, m is a number from 0 to the valence of the metal, and m plus must equal the valence of the metal, wherein said organometallic compound has been vaporized at a temperature in the range of about room temperature to about 100° C.;

(c) exposing said substrate to hydrogen gas at a temperature in the range of about room temperature to about 100° C.;

(d) reacting said organometallic compound with said hydrogen gas for a time sufficient to cause a layer of said metal to form on the surface of said substrate and catalytically hydrogenate said hydrocarbon ligands of said organometallic compound without causing substantial impurities from said hydrocarbon ligands of said organometallic compound to be formed on said surface with said metal layer.

2. The process of claim 1, wherein said metal is selected from the group consisting of metals having an atomic number between 22 and 29, 40 and 47 or 72 and 79.

3. The process of claim 2, wherein said metal is selected from the group consisting of metals having an atomic number between 25 and 29, 42 and 47 and 74 and 79.

4. The process of claim 3, wherein said metal is selected from the group consisting of cobalt, rhodium, iridium, nickel, palladium, platinum, copper, silver, gold and tungsten, 5. The process of claim 1, wherein said organometallic compound has a vapor pressure of at least 0.005 torr between 25° and 50° C.

6. The process of claim 1 wherein said organometallic compound is selected from the group consisting of:

CpPtMe$_3$; CpPt(allyl); CpPt(methylallyl); MeCpPt(methylally;
bisallylPd; (methylallyl)Pd(allyl); bis(2-methylally)-palladium; (cyclopentadienyl)(allyl)palladium;
(CH$_3$C$_5$H$_4$)PtMe$_3$; (C$_3$H$_5$)$_3$Rh; (C$_3$H$_5$)$_3$Ir; CpIr(hexadiene);
(C$_5$H$_5$)Ir(C$_6$H$_8$); (C$_5$(CH$_3$)$_5$)Ir(ethylene)$_2$; (C$_5$H$_7$)Ir(C$_8$H$_8$);
(CH$_3$C$_5$H$_4$)$_2$Ni;
(C$_5$H$_5$)CoCh; (CH$_3$C$_5$H$_4$)Co(MeCp); (cyclobutadienyl)(cyclopentadienyl)cobalt, C$_4$H$_3$CoC$_5$H$_5$;
bis(cyclopentadienyl)cobalt; (C$_5$H$_5$)$_2$Co; bis(methylcyclopentadienyl)cobalt, (CH$_3$C$_5$H$_4$)$_2$Co; cyclopentadienyl(1,3-hexadienyl)cobalt, C$_5$H$_5$CoC$_6$H$_7$;

(cyclopentadienyl)(5-methyl-cyclopentadienyl)cobalt,
$C_5H_5CoC_5H_4CH_3$;
bis(ethylene)(pentamethylcyclopentadienyl)cobalt, $(CH_3)_5C_5Co(C_2H_2)_2$; triallylchromium, $(C_3H_4)_3Cr$;
bis(cyclopentadienyl)chromium, $(C_5H_5)_2Cr$;
(cycloheptatrienyl)(cyclopentadienyl)chromium, $C_7H_7CrC_5H_5$;
bis(cyclopentadienyl)iron, $(C_5H_5)_2Fe$; (2,4-cyclohexadienyl)(cyclopentadienyl)iron, $C_6H_7FeC_5H_5$;
(cyclopentadienyl)(methylcyclopentadienyl)iron, $C_5H_5FeC_5H_4CH_3$; bis(methylcyclopentadienyl)iron, $(CH_3C_5H_4)_2Fe$;
(cycloheptatrienyl)(cyclopentadienyl)manganese, $C_5H_5MnC_7H_8$;
(benzene)(cyclopentadienyl)manganese, $C_5H_5MnC_6H_6$;
bis(cyclopentadienyl)dihydromolybdenum, $(C_5H_5)_2MoH_2$;
bis(cyclopentadienyl)(ethylene)molybdenum, $(C_5H_5)_2MoC_2H_2$;
tris(butadienyl)molybdenum, $(C_4H_4)_3Mo$;
dicylopentadienyltrihydronobium, $(C_5H_5)_2NbH_3$;
bis(cyclopentadienyl)niobiumborohydride, $(C_5H_5)_2NbH_2BH_2$;
bis(cyclopentadienyl)hydro(ethylene)niobium, $(C_5H_5)_2NbHC_2H_2$;
bis(cyclopentadienyl)allylniobium, $(C_5H_5)_2NbC_3H_4$;
ethenylosmocene, $C_5H_5OsC_5H_4CHCH_2$; 1,1'-dimethylosmocene, $(C_5H_4CH_3)_2Os$; ethylosmocene, $C_5H_5OsC_5H_4CH_2CH_3$;
bis(cyclopentadienyl)hydridorhenium, $(C_5H_5)_2ReH$;
hexamethylrhenium, $(CH_3)_6Re$;
cyclopentadienyl(methylcyclopentadienyl)ruthenium, $C_5H_5RuC_5H_4CH_3$; ruthenocenylacetylene, $C_5H_5RuC_5H_4CCH$;
ethenylruthenocene, $C_5H_5RuC_5H_4CHCH_2$;
bis(methylcyclopentadienyl)ruthenium, $RU(CH_3C_5H_4)_2$;
ethylruthenocene, $C_5H_5RuC_5H_4CH_2CH_3$; pentamethyltantalum, $Ta(CH_3)_5$; bis(cyclopentadienyl)trihydrotantalum, $(C_5H_5)_2TaH_3$; bis(cyclopentadienyl)trimethyltitanium, $(C_5H_4)_2Ti(CH_3)_3$; titanocene borohydride, $(C_5H_5)_2TiH_2BH_2$;
bis(cyclopentadienyl)dimethyltitanium, $(C_5H_5)_2Ti(CH_3)_2$;
bis-(cyclopentadienyl)methylvanadium, $(C_5H_5)_2VCH_3$; 1,1'-dimethylvanadocene, $(C_5H_4CH_3)_2V$; bis(2,4-dimethylpentadienyl)vanadium, $(CH_5H_3(CH_3)_2)_2V$;
bis(cyclopentadienyl)dihydrotungsten, $(C_5H_5)_2WH_2$; trisbutadiennyltungsten, $(C_4H_5)_3W$; and bis(cyclopentadienyl(butadienyl)zirconium, $(C_5H_5)_2ZrC_4H_4$.

7. The process of claim 6, wherein said organometallic compound is selected from the group consisting of: $CpPtMe_3$, $(CH_3C_5H_4)PtMe_3$, $(C_3H_5)_3Rh$, $(C_3H_5)_3Ir$, $HRe(CO)_5$, $(CH_3C_5H_4)_2Ni$, $(C_5H_5)Co(CO)_2$, $(C_5H_5)CoCp$, $(C_5H_5)CoCh$, and $(CH_3C_5H_4)Co(Mecp)$.

8. The process of claim 1 wherein said organometallic compound is $CpPtMe_3$ or $MeCpPtMe_3$.

9. The process of claim 1, wherein said substrate comprises silicon.

10. The process of claim 4, wherein said substrate comprises silicon.

11. The process of claim 6, wherein said substrate comprises silicon.

12. The process of claim 8, wherein said substrate comprises silicon.

13. The process of claim 12, wherein said substrate further comprises tungsten and said organometallic compound is selectively deposited thereon.

14. The process of claim 13, wherein said organometallic compound is $CpPtMe_3$.

15. The process of claim 1 further comprising the step of:
(d) elevating the temperature of said substrate to facilitate elimination of the organic portion of said organometallic compound that has formed on the surface of said substrate.

16. The process of claim 1 wherein said layer of metal formed on the surface of said substrate includes at most 3.5% carbon as an impurity, and said organometallic compound has a vapor pressure of at least 0.001 torr within the temperature range of about 25°-100° C.

17. The process of claim 1, wherein said metal is selected from the group consisting of metals having an atomic number between 25 and 29, 42 and 47 or 74 and 79.

18. The process of claim 17, wherein said metal is selected from the group consisting of cobalt, rhodium, iridium, nickel, palladium, platinum, copper, silver, gold and tungsten.

19. A process for depositing on at least a part of a substrate, at least one metal that can readily cycle between two oxidation states and is a hydrogenation catalyst capable of hydrogenating hydrocarbon ligands of an organometallic compound comprising the steps of:
(a) maintaining said substrate within a reaction zone at a temperature in the range of about room temperature to about 190° C.;
(b) exposing said substrate to a gas mixture containing an inert gas admixed with at least one organometallic compound vaporized at a temperature in the range of about room temperature to about 100° C. and having the formula $L_nMR_m$, where L is hydrogen, ethylene, allyl, methylallyl, butadienyl, pentadienyl, cyclopentadienyl, methylcyclopentadienyl, cyclohexadienyl, hexadienyl, cycloheptatrienyl, or derivatives of said compounds having at least one alkyl side chain having less than five carbon atoms, M is a metal that can readily cycle between two oxidation states and can catalyze hydrogenation of hydrocarbon ligands of said organometallic compound, R is methyl, ethyl, propyl, or butyl, n is a number from 0 to the valence of said metal, m is a number from 0 to the valence of the metal, and m plus n must equal the valence of the metal;
(c) exposing said substrate to hydrogen gas;
(d) irradiating said reaction zone with a laser beam at a wavelength and for a time which is sufficient to cause said organometallic compound to react and, said metal film on the surface of said substrate in the presence of hydrogen without causing substantial impurities from the hydrocarbon ligands of said organometallic compound to be formed on said surface.

20. The process of claim 19 wherein said metal film includes at most 3.5% carbon as an impurity.

21. The process of claim 19, wherein said organometallic compound is $CpPtMe_3$ or $MeCpPtMe_3$.

22. The process of claim 19, wherein said substrate comprises silicon.

23. The process of claim 19, wherein said metal is selected from the group consisting of metals having an atomic number between 22 and 29, 40 and 47 or 72 and 79.

24. The process of claim 19, wherein said organometallic compound is selected from the group consisting of: $CpPtMe_3$; $(CH_3C_5H_4)PtMe_3$, $(C_3H_5)_3Rh$, $(C_3H_5)_3Ir$, $HRe(CO)_5$, $(CH_3C_5H_4)_2Ni$, $(C_5H_5)Co(CO)_2$, $(C_5H_5)CoCp$, $(C_5H_5)CoCh$, and $(CH_3C_5H_4)Co(Mecp)$.

25. The process of claim 24, wherein said substrate comprises silicon.

26. The process of claim 25, wherein said organometallic compound is selected from the group consisting of $CpPtMe_3$ and $MeCpPtMe_3$.

27. A process for selectively depositing at least one metal on a substrate which comprises at least two areas of differing chemical composition, wherein said metal can readily cycle between two oxidation states and is a hydrogenation catalyst capable of hydrogenating hydrocarbon ligands of an organometallic compound comprising the steps of:

(a) exposing said substrate to a gas mixture containing an inert gas and a vaporized organometallic compound having the formula $L_nMR_m$, where L is hydrogen, ethylene, allyl, methylallyl, butadienyl, pentadienyl, cyclopentadienyl, methylcyclopentadienyl, cyclohexadienyl, hexadienyl, cycloheptatrienyl, or derivatives of said compounds having at least one alkyl side chain having less than five carbon atoms, M is a metal which can readily cycle between two oxidation states and is a hydrogenation catalyst capable of hydrogenating hydrocarbon ligands of an organometallic compound, R is methyl, ethyl, propyl, or butyl, n is a number from 0 to the valence of said metal, m is a number from 0 to the valence of said metal, and m plus n must equal the valence of the metal, which organometallic compound has been vaporized at a temperature within the range of about room temperature to about 100° C.;

(b) exposing said substrate to hydrogen gas at a temperature in the range of about room temperature to about 100° C.; and (c) maintaining said substrate at a temperature in the range of about room temperature to about 190° C. to cause said organometallic compound to react with said hydrogen on said substrate on an area of a first chemical composition by reducing said organometallic compound on said substrate such that said metal is deposited without substantial impurities caused by the organic portion of said organometallic compound, and to avoid depositing said metal on an area of a second chemical composition.

28. The process of claim 27, wherein said organometallic compound is selected from the group consisting of $CpPtMe_3$ and $MeCpPtMe_3$.

29. The process of claim 27, wherein said substrate comprises a first area comprising tungsten and a second area not comprising tungsten.

30. The process of claim 27 wherein said metal includes at most 3.5% carbon as an impurity.

* * * * *